US012620169B2

(12) United States Patent
Zagorchev

(10) Patent No.: US 12,620,169 B2
(45) Date of Patent: May 5, 2026

(54) DENSE NON-RIGID VOLUMETRIC MAPPING OF IMAGE COORDINATES USING SPARSE SURFACE-BASED CORRESPONDENCES

(71) Applicant: ClearPoint Neuro, Inc., Solana Beach, CA (US)

(72) Inventor: Lyubomir Zagorchev, Burlington, MA (US)

(73) Assignee: ClearPoint Neuro, Inc., Solana Beach, CA (US)

( * ) Notice: Subject to any disclaimer, the term of this patent is extended or adjusted under 35 U.S.C. 154(b) by 109 days.

(21) Appl. No.: 18/410,711

(22) Filed: Jan. 11, 2024

(65) Prior Publication Data

US 2024/0242426 A1    Jul. 18, 2024

Related U.S. Application Data

(60) Provisional application No. 63/479,733, filed on Jan. 12, 2023.

(51) Int. Cl.
*G06T 17/00*        (2006.01)
*A61B 90/00*        (2016.01)
*G06T 7/00*        (2017.01)

(52) U.S. Cl.
CPC ............ *G06T 17/00* (2013.01); *A61B 90/361* (2016.02); *G06T 7/0012* (2013.01); (Continued)

(58) Field of Classification Search
CPC .................. G06T 17/00; G06T 7/0012; G06T 2207/10081; G06T 2207/10088; (Continued)

(56) References Cited

U.S. PATENT DOCUMENTS 7,072,705 B2 *    7/2006    Miga .......................... G06T 7/35
                                                                    600/411
8,768,022 B2 *    7/2014    Miga ....................... G06T 7/344
                                                                    382/128

(Continued)

FOREIGN PATENT DOCUMENTS

WO    WO-2017180097 A1 *    10/2017    ............. G06T 7/344

OTHER PUBLICATIONS

Zollhofer,M. et al "Real-time Non-rigid Reconstruction using RGB-D Camera" ACM Transactions on Graphics (2014) vol. 33 No. 4 pp. 1-12 (Year: 2014).*

(Continued)

*Primary Examiner* — Temesghen Ghebretinsae
(74) *Attorney, Agent, or Firm* — Sheppard Mullin Richter & Hampton LLP

(57)    ABSTRACT

Examples of the presently disclosed technology provide systems and methods for improved image registration for image-guided brain interventions. The disclosed systems and methods use sparse surface-based correspondences between vertices of patient-specific 3D mesh representations to fit a non-rigid transformation function for estimating a deformation field that maps one cranial image (e.g., a source image used for surgical trajectory planning) to another cranial image (e.g., a reference image obtained during an image-guided brain intervention).

20 Claims, 8 Drawing Sheets

(52) U.S. Cl.
CPC .............. *G06T 2207/10081* (2013.01); *G06T 2207/10088* (2013.01); *G06T 2207/10104* (2013.01); *G06T 2207/30016* (2013.01)

(58) Field of Classification Search
CPC . G06T 2207/10104; G06T 2207/30016; G06T 7/33; A61B 90/361; A61B 34/10; A61B 2034/105
See application file for complete search history.

(56) References Cited

U.S. PATENT DOCUMENTS

| | | | | |
|---|---|---|---|---|
| 10,896,507 | B2 * | 1/2021 | Burris ................... | G06T 7/0014 |
| | | | | 382/128 |
| 2014/0161338 | A1 * | 6/2014 | Machado ................ | G06T 7/344 |
| | | | | 382/131 |
| 2019/0087957 | A1 * | 3/2019 | Burris ................ | A61B 5/02014 |
| | | | | 382/128 |
| 2019/0336109 | A1 * | 11/2019 | Pheiffer ................... | G06T 7/37 |
| | | | | 600/438 |
| 2022/0401148 | A1 * | 12/2022 | Siemionow .......... | A61B 90/361 |
| | | | | 382/128 |
| 2024/0153031 | A1 * | 5/2024 | Zhou ........................ | G06T 3/18 |
| | | | | 382/128 |

OTHER PUBLICATIONS

Bozic A et al. "Deepdeform: Learning non rigid RGB-D reconstruction with semi-supervised data" CVPR (2020);7002-7012 (Year: 2020).*

* cited by examiner

300

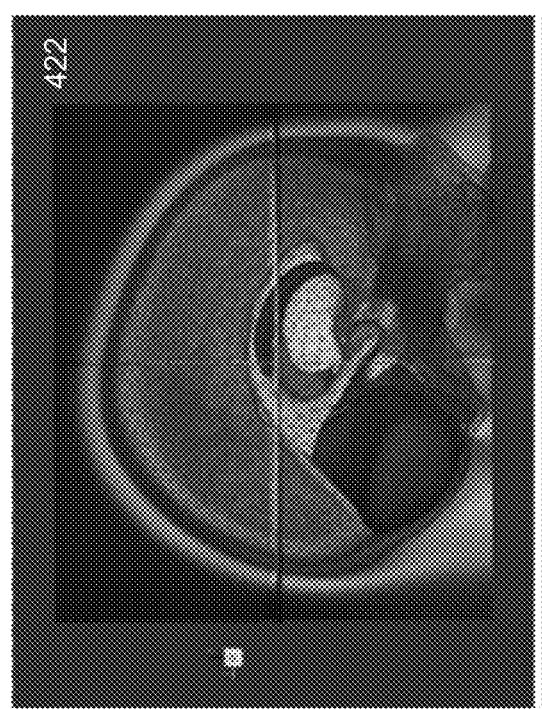
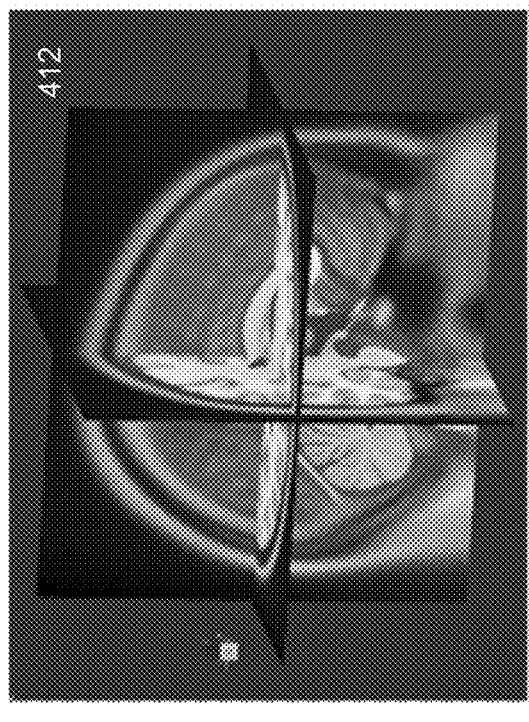
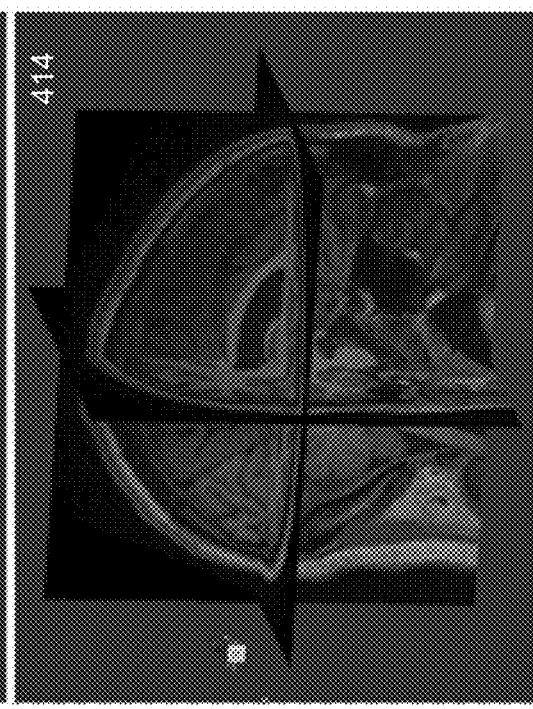
Fig. 4

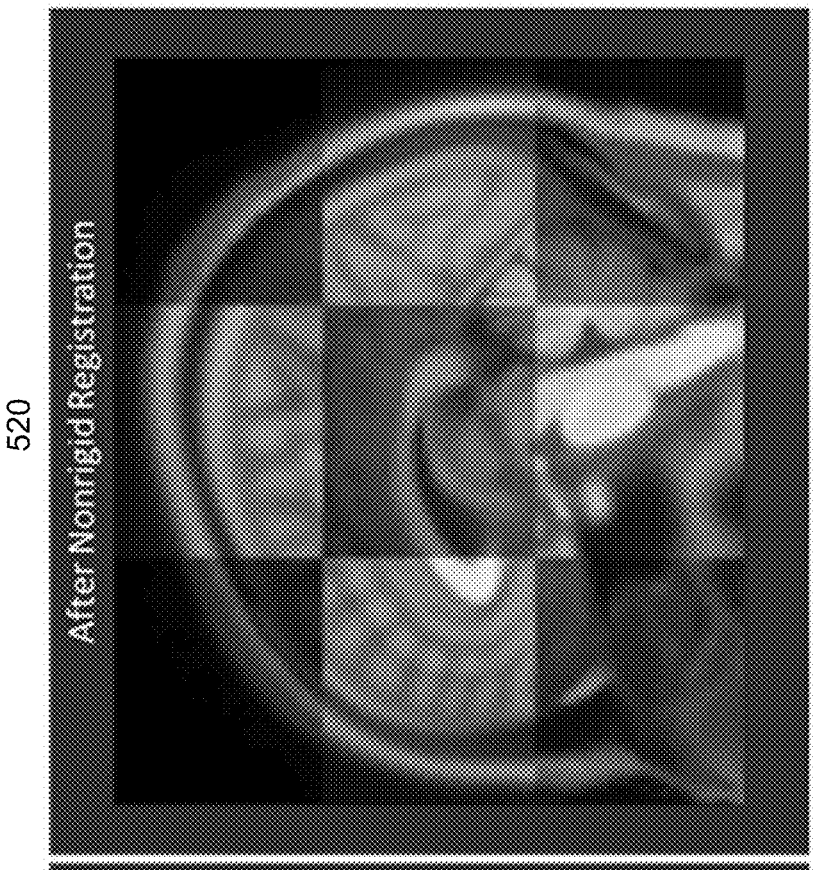
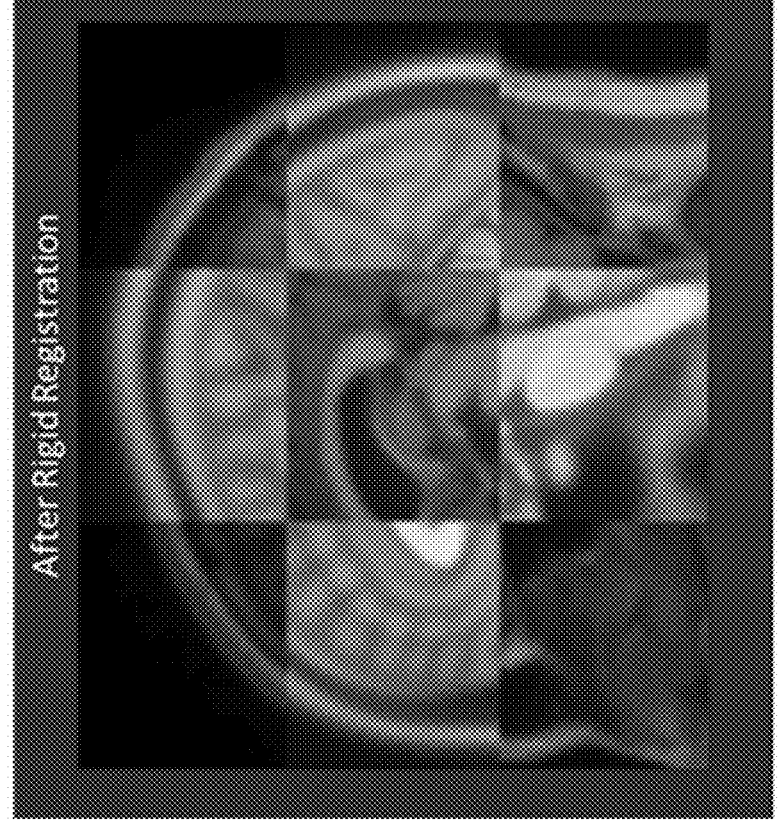
Fig. 5

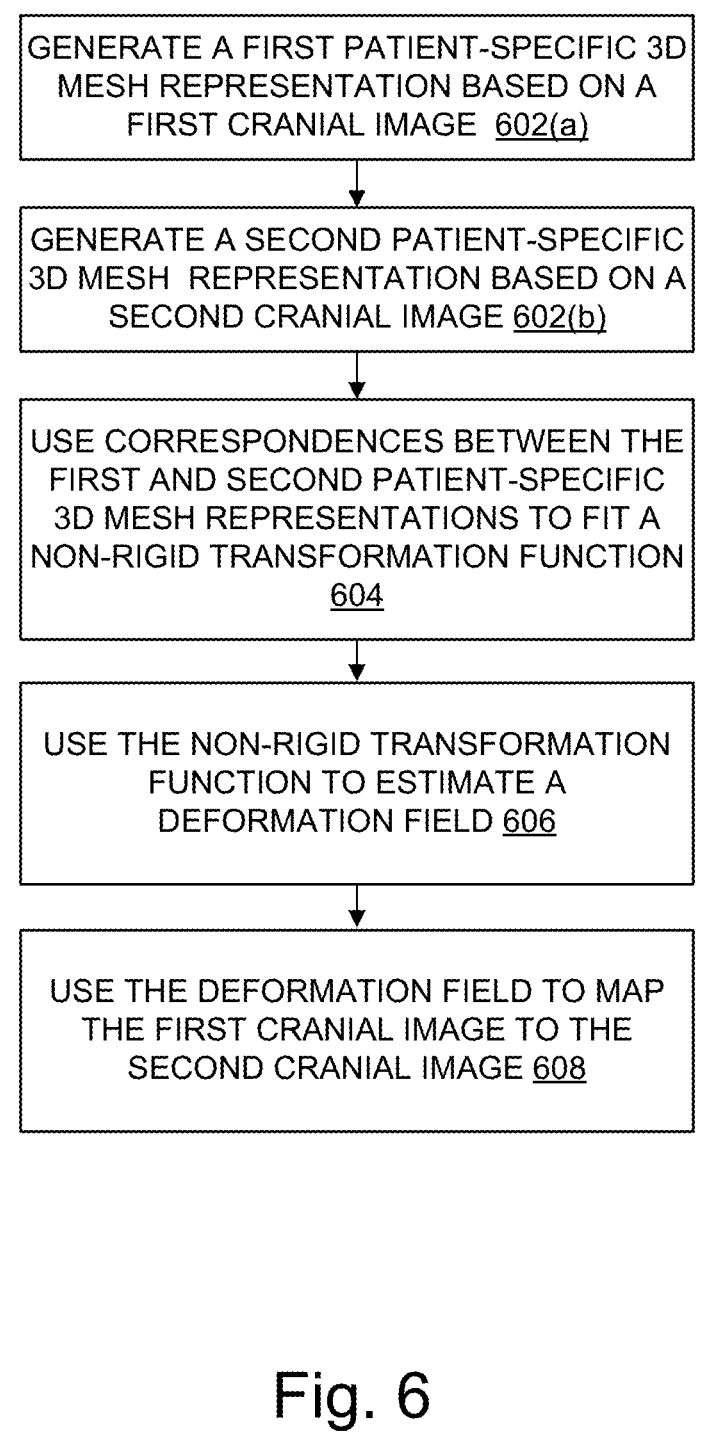

GENERATE A FIRST PATIENT-SPECIFIC 3D MESH REPRESENTATION BASED ON A FIRST CRANIAL IMAGE 602(a)

GENERATE A SECOND PATIENT-SPECIFIC 3D MESH REPRESENTATION BASED ON A SECOND CRANIAL IMAGE 602(b)

USE CORRESPONDENCES BETWEEN THE FIRST AND SECOND PATIENT-SPECIFIC 3D MESH REPRESENTATIONS TO FIT A NON-RIGID TRANSFORMATION FUNCTION 604

USE THE NON-RIGID TRANSFORMATION FUNCTION TO ESTIMATE A DEFORMATION FIELD 606

USE THE DEFORMATION FIELD TO MAP THE FIRST CRANIAL IMAGE TO THE SECOND CRANIAL IMAGE 608

Fig. 6

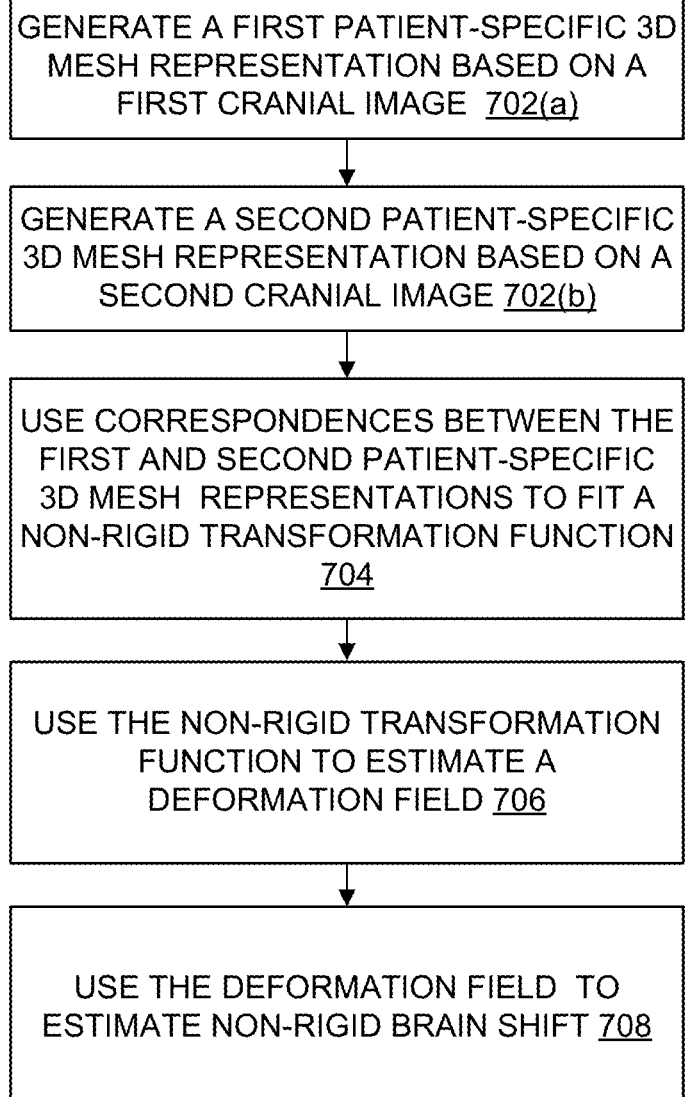

GENERATE A FIRST PATIENT-SPECIFIC 3D MESH REPRESENTATION BASED ON A FIRST CRANIAL IMAGE  702(a)

GENERATE A SECOND PATIENT-SPECIFIC 3D MESH REPRESENTATION BASED ON A SECOND CRANIAL IMAGE 702(b)

USE CORRESPONDENCES BETWEEN THE FIRST AND SECOND PATIENT-SPECIFIC 3D MESH  REPRESENTATIONS TO FIT A NON-RIGID TRANSFORMATION FUNCTION 704

USE THE NON-RIGID TRANSFORMATION FUNCTION TO ESTIMATE A DEFORMATION FIELD 706

USE THE DEFORMATION FIELD  TO ESTIMATE NON-RIGID BRAIN SHIFT 708

Fig. 7

DENSE NON-RIGID VOLUMETRIC MAPPING OF IMAGE COORDINATES USING SPARSE SURFACE-BASED CORRESPONDENCES

REFERENCE TO RELATED APPLICATION

The present application claims priority to U.S. Provisional Patent Application No. 63/479,733, filed Jan. 12, 2023, and titled "DENSE NON-RIGID VOLUMETRIC MAPPING OF IMAGE COORDINATES USING SPARSE SURFACE-BASED CORRESPONDENCE," which is incorporated herein by reference in its entirety.

TECHNICAL FIELD

The present disclosure relates generally to medical technologies, and more particularly, some examples relate to non-rigid volumetric mapping for cranial images.

BACKGROUND

Image registration may refer to a computational method for determining a spatial transformation that maps one image (sometimes referred to as a "source or moving image") to another image (sometimes referred to as a "reference or fixed image") point-by-point (or more specifically, voxel-by-voxel for 3D images). Image registration can be either rigid or non-rigid. Rigid registration preserves distance between image points and involves only rotation and translation. By contrast, non-rigid registration is spatially unconstrained and in addition to rotation and translation may involve at least some "stretching" of images (here distances between image points of a stretched image may not be preserved).

Image registration (rigid or non-rigid) typically utilizes a deformation field (i.e., a geometric transformation) to map features of a source/moving image to features in a reference/fixed image. In dense image registrations, the deformation field assigns a displacement vector to each image point of a source image. The displacement vector for a given point of a source image maps the given point to its corresponding spatial location in the reference image.

BRIEF DESCRIPTION OF THE DRAWINGS

The present disclosure, in accordance with one or more various examples, is described in detail with reference to the following figures. The figures are provided for purposes of illustration only and merely depict examples.

FIG. 4 depicts adaption of a shape-constrained deformable cranial region model to two example cranial images, in accordance with examples of the presently disclosed technology.

FIG. 5 depicts a first example checkerboard overlay of two cranial images after rigid registration, and a second example checkerboard overlay of the two cranial images after non-rigid registration performed in accordance with the presently disclosed technology.

FIG. 6 depicts an example flow diagram that may be used to non-rigidly transform a first cranial image to a second cranial image, in accordance with various examples of the presently disclosed technology.

FIG. 7 depicts an example flow diagram that may be used to detect/estimate non-rigid brain shift during a brain intervention using an estimated deformation field, in accordance with various examples of the presently disclosed technology.

The figures are not exhaustive and do not limit the present disclosure to the precise form disclosed.

DETAILED DESCRIPTION

In image-guided brain interventions, image registration can be used to align (in the same image space) cranial images acquired at different times (e.g., pre-operative vs. intra-operative) or using different modalities (e.g., a brain atlas, MR, computerized tomography (CT), positron emission tomography (PET), etc.).

In conventional image-guided brain interventions, rigid registration is used to reduce differences in position and orientation across cranial images. An example overlay of two cranial images before image registration is shown in the third row of FIG. 1. An example overlay of the two cranial images after rigid registration is illustrated in the third row of FIG. 2. As depicted, rigid registration can bring the two cranial images into approximate alignment, but it can be less effective in aligning images of soft (brain) tissues within the skull. This misalignment of soft tissue images can result from "non-rigid brain shift" during a surgical intervention.

Non-rigid brain shift may refer to a deformation/shift of soft tissues of the brain that is more complex than mere rotation or translation. During a surgical intervention into the brain, non-rigid brain shift may result from various causes including cerebrospinal fluid (CSF) leakage, a change in intercranial pressure, etc.

Figure 2:
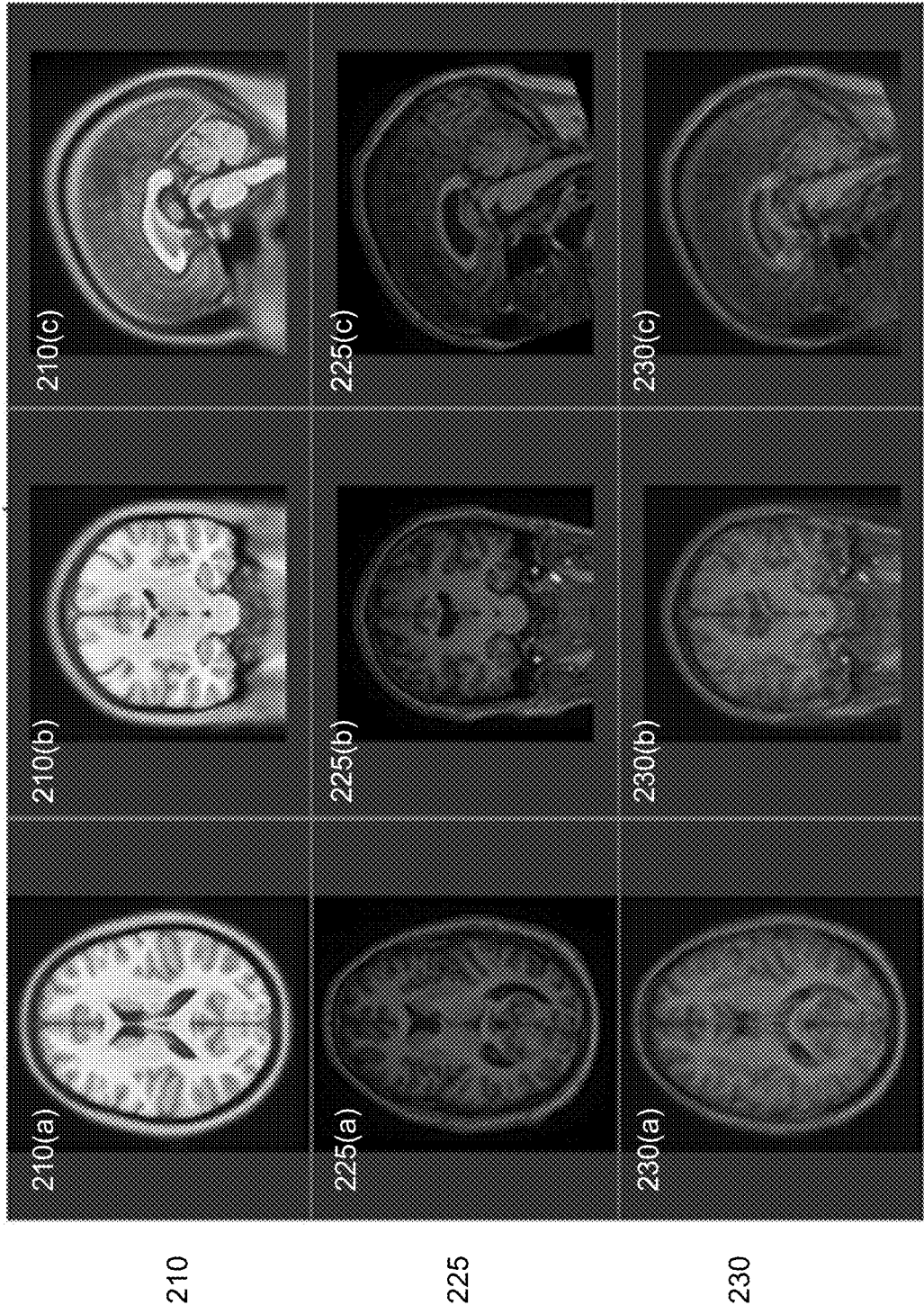
FIG. 2 depicts cross sections of an overlay of two example MR cranial region images after rigid registration, in accordance with various examples of the presently disclosed technology.

As alluded to above (and as depicted in FIG. 2), rigid registrations have trouble accounting for non-rigid brain shift. In other words, even after a rigid registration, images of soft brain tissues in a rigidly transformed source image may not closely align with images of the soft brain tissues in a reference image. Where planned target and entry points for surgical trajectories are located on/within the soft tissues of a patient's brain, this misalignment can cause problems as coordinates for these planned target/entry points may shift in space with respect to their location in a cranial image that was used for planning (e.g., a pre-operative image of a patient, a brain atlas, etc.).

While non-rigid registration can improve alignment between soft tissue images of two cranial images after non-rigid brain shift has occurred, existing non-rigid registration techniques used in conjunction with image-guided brain interventions have certain drawbacks. In particular, these existing techniques—which typically involve using image intensities (or their derivatives) to align two images non-rigidly—can be slow and generally cannot be applied to multi-modal data/images (i.e., they generally would not be able to register/align two different types of images, such as an MR image with a CT image).

Against this backdrop, examples of the presently disclosed technology provide rapid non-rigid image registration systems and methods for image-guided brain interventions that can be applied to multi-modal data. The disclosed systems and methods use correspondences between patient-specific 3D mesh representations to fit a non-rigid transformation function that can be used for estimating a deformation field that maps one cranial image (e.g., a source image obtained during surgery) to another cranial image (e.g., a reference image that was used for surgical trajectory planning, such as a pre-operative image of a patient or a brain atlas). In various implementations, the above-referenced correspondences may comprise surface-based correspondences between mesh vertices of the patient-specific 3D mesh representations. Such surface-based correspondences may be termed "sparse" because the mesh vertices comprise a "sparse" subset of points of a 3D image. Using a "sparse" subset of points to fit the non-rigid transformation function, examples can perform non-rigid registrations faster than existing image intensity-based non-registration techniques which perform iterative optimizations over an entire 3D image.

For instance, examples can generate a first patient-specific 3D mesh representation by adapting a shape-constrained deformable cranial region model to a first cranial image. The shape-constrained deformable cranial region model may comprise a computerized 3D mesh representation of a non-patient-specific human head that preserves point-based correspondences during mesh adaption to patient specific images. The first cranial image may comprise an MR or CT image obtained prior to surgery that was used for surgical trajectory planning. In certain other implementations, the first cranial image may comprise a brain atlas that was used for surgical trajectory planning.

Examples can then generate a second patient-specific 3D mesh representation by adapting the shape-constrained deformable cranial region model to a second cranial image (e.g., a second MR or CT image obtained during surgery). Upon generating the two patient-specific 3D mesh representations, examples can use correspondences between the patient-specific 3D mesh representations (e.g., "sparse" surface-based correspondences between mesh vertices of the patient-specific 3D mesh representations) to fit a non-rigid transformation function. Examples can then use the non-rigid transformation function to estimate a deformation field that provides displacement vectors for mapping points/voxels of the first cranial image to their corresponding locations/points in the second cranial image. Examples can use this deformation field to transform/map the first cranial image to the second cranial image point-by-point/voxel-by-voxel. In certain implementations, this may comprise mapping coordinates of planned surgical target points and entry points from the first cranial image to the second cranial image.

In various implementations, examples can also be used to detect non-rigid brain shift or other problematic conditions that result in non-rigid deformation of the brain. For instance, examples can detect non-rigid brain shift based on the estimated deformation field. In various implementations, this may comprise determining the size and location of displacement vectors used to map points/voxels of the first cranial image to their respective locations/points in the second cranial image, and comparing those values to corresponding threshold values. Here, detecting non-rigid brain shift can improve patient safety because in many cases the causes of non-rigid brain shift (e.g., CSF leakage or a change in intracranial pressure) can be harmful to the patient—and early/accurate detection may reduce patient harm. Moreover, through analysis of the estimated deformation field (e.g., analyzing the relative size and location of displacement vectors used to map points/voxels of the first cranial image to their respective locations/points in the second cranial image), examples can identify specific locations of a patient's brain impacted most by non-rigid brain shift—and by extension, locations of the patient's brain which may be most impacted by the condition that caused the non-rigid brain shift. Here, such pin-pointed detection may further improve patient safety/reduce patient harm.

Examples of the presently disclosed technology provide numerous advantages over existing image registration technologies used in conjunction with image-guided brain surgeries.

For instance, as compared to the rigid registration techniques conventionally used in image-guided brain interventions, examples can improve alignment between soft tissue images of cranial images obtained before and after non-rigid brain shift has occurred. This may include more accurate/precise mapping of planned target and entry coordinates from a first cranial image (e.g., a pre-operative image or brain atlas used for surgical trajectory planning) to their corresponding locations in a second cranial image (e.g., an intra-operative cranial image obtained during an image-guided brain intervention). By accurately/precisely mapping planned target and entry point coordinates to their appropriate locations in cranial images obtained during surgery, examples can improve safety and efficacy for image-guided brain surgeries (e.g., by ensuring that target and entry point coordinates in intra-operative cranial images are located approximately in their planned locations), reduce surgical intervention times, etc.

Examples also provide a technical improvement over other non-rigid registration techniques that could be used in conjunction with image-guided surgical interventions into the brain. For instance, where examples utilize "sparse" surface-based correspondences of patient-specific 3D mesh representations, examples can perform non-rigid registrations faster than existing image intensity-based techniques which perform iterative optimizations over an entire 3D image (as alluded to above, these surface-based correspondences can be termed "sparse" because mesh vertices comprise a "sparse" subset of points of a 3D image). Also, unlike existing non-rigid registration techniques, examples of the presently disclosed technology can be applied to multi-modal images (e.g., they can align a CT image with an MR image). This feature of the presently disclosed technology can be important where e.g., a pre-operative image used for surgical planning is obtained using one type of imaging technology (e.g., CT) and intra-operative images are obtained using another type of imaging technology (e.g., MR).

Also, and as alluded to above, through use of non-rigid image registration, examples can detect and/or estimate non-rigid brain shift precisely. Here, precise detection/estimation of non-rigid brain shift can improve patient safety because in many cases the causes of non-rigid brain shift (e.g., CSF leakage or a change in intracranial pressure) can be harmful to the patient—and early/accurate detection may reduce patient harm.

Figure 1:
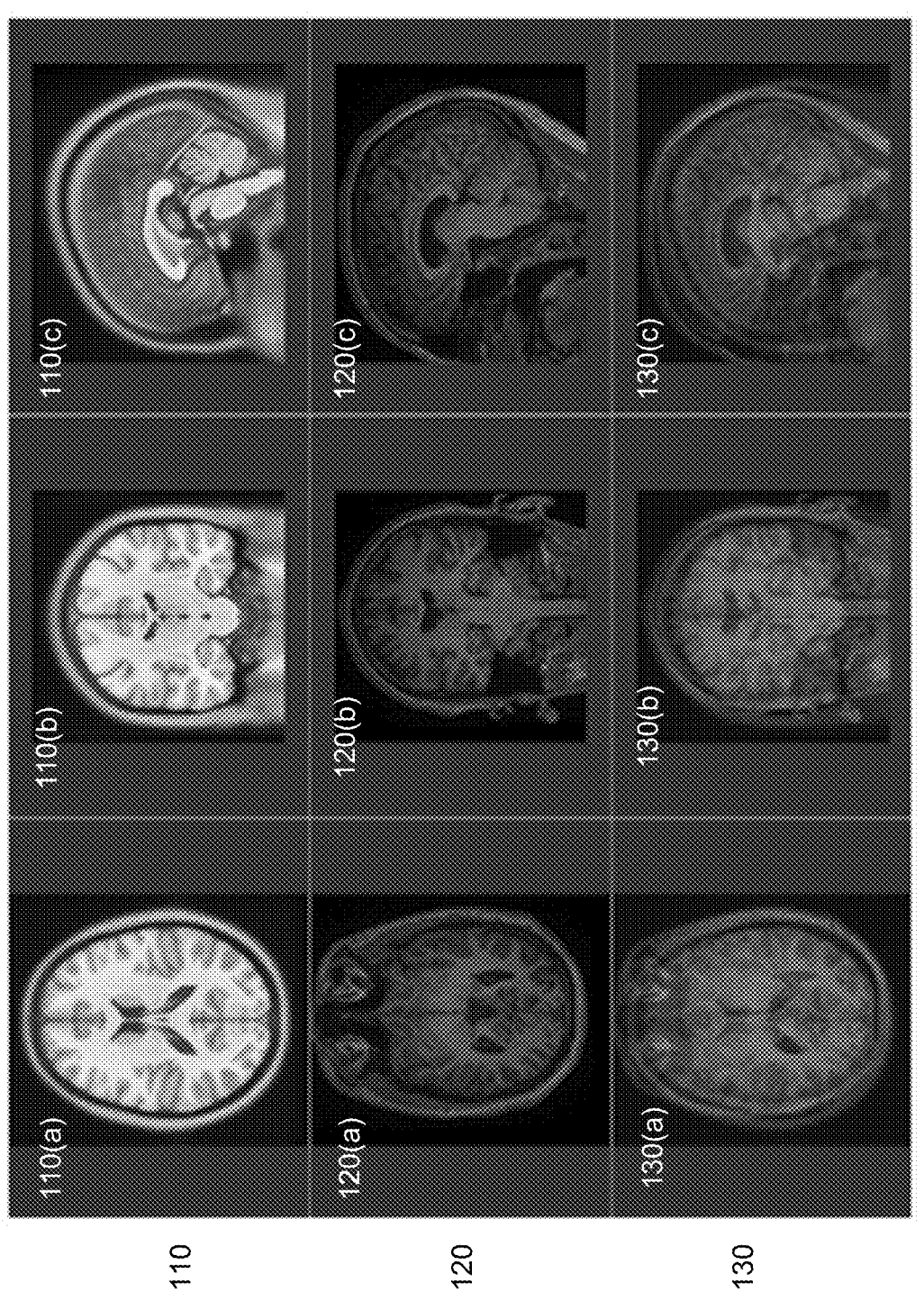
FIG. 1 depicts cross sections of an overlay of two example cranial images without image registration, in accordance with various examples of the presently disclosed technology.

FIG. 1 depicts cross sections of an overlay of two example cranial images without image registration, in accordance with various examples of the presently disclosed technology.

In particular, images 110(a), 110(b), and 110(c) depict axial, coronal, and sagittal cross sections respectively of an image 110 of a cranial region (i.e., any one or combination of scalp, skull, brain, head, etc.). In certain implementations, image 110 may comprise a brain atlas (e.g., a generalized 3D map of a brain). In other implementations, image 110 may comprise a pre-operative or inter-operative image of a patient's brain obtained using imagining technologies such as MR, CT, PET, etc.

Images 120(*a*), 120(*b*), and 120(*c*) depict axial, coronal, and sagittal cross sections respectively of an image 120 of a cranial region. In certain implementations, image 120 may comprise a brain atlas. In other implementations, image 120 may comprise a pre-operative or inter-operative image of a patient's brain obtained using imagining technologies such as MR, CT, PET, etc. In certain of these implementations, image 120 and image 110 may be pre-operative and inter-operative images of the same patient's cranial region (or vice versa). In other implementations, image 110 and image 120 may comprise images of different patients' cranial regions prior to, or during surgery.

Images 130(*a*), 130(*b*), and 130(*c*) depict axial, coronal, and sagittal cross sections respectively of an overlay 130 of image 110 and image 120 in the same image space (i.e., a common coordinate system). Image registration has not been performed prior to creating/generating overlay 130.

As depicted, images of the scalp, skull, and brain regions are misaligned in overlay 130. As alluded to above, in certain examples this misalignment may result from rigid movements of a patient between when image 110 and image 120 were obtained (e.g., rotation or translation of the patient's head).

As alluded to above, one of the goals of image registration is to improve alignment between images. Image alignment (or lack thereof) can be illustrated using overlays such as overlay 130. In the context of image-guided surgical interventions into the brain, improving image alignment between (a) a cranial image used for planning target point and entry point coordinates (e.g., a pre-operative image or a brain atlas); and (b) subsequently obtained intra-operative cranial images (which may be obtained after non-rigid brain shift)—can improve the safety and efficacy of planned surgical procedures. For example, safety and efficacy can be improved by more accurately/precisely mapping coordinates of planned target points and entry points from a cranial image used for surgical trajectory planning to their corresponding/appropriate locations in an intra-operative cranial image. In other words, non-rigid image alignment can better account for shifting locations of target and entry point coordinates during surgery. As alluded to above, by providing systems and methods for non-rigid image alignment/registration for image-guided brain interventions, examples can improve safety and efficacy of planned surgical procedures, reduce surgical intervention times, etc.

FIG. 2 depicts cross sections of an overlay of two example cranial images after rigid registration, in accordance with various examples of the presently disclosed technology.

In particular, images 210(*a*), 210(*b*), and 210(*c*) depict axial, coronal, and sagittal cross sections respectively of an image 210 of a cranial region (i.e., any one or combination of scalp, skull, brain, head, etc.). In certain implementations, image 210 may comprise a brain atlas (e.g., a generalized 3D map of a brain). In other implementations, image 210 may comprise a pre-operative or inter-operative image of a patient's brain obtained using imagining technologies such as MR, CT, PET, etc. In some implementations, image 210 may be the same as image 110 of FIG. 1.

Images 225(*a*), 225(*b*), and 225(*c*) depict axial, coronal, and sagittal cross sections respectively of a rigidly transformed image 225 of a cranial region. As alluded to above, rigidly transformed image 225 may have been rigidly transformed to better align with image 210. In some examples, image 225 may be a rigidly transformed version of an image

220 (not depicted). In certain implementations, image 220 may comprise a brain atlas. In other implementations, image 220 may comprise a pre-operative or inter-operative image of a patient's brain obtained using imagining technologies such as MR, CT, PET, etc. In certain of these implementations, image 220 and image 210 may be pre-operative and inter-operative images of the same patient's cranial region (or vice versa). In other implementations, image 210 and image 220 may comprise images of different patients' cranial regions prior to, or during surgery. In some implementations, image 220 may be the same as image 120 of FIG. 1.

Images 230(*a*), 230(*b*), and 230(*c*) depict axial, coronal, and sagittal cross sections respectively of an overlay 230 of image 210 and rigidly transformed image 225 in the same image space. As alluded to above, rigid registration (e.g., rigid transformation of an image 220 to align with image 210) has been performed prior to creating/generating overlay 230.

As depicted in overlay 230, images of the scalp and skull are in approximate alignment after rigid registration. However, the soft tissues images are misaligned (in particular, overlay 230 includes significant image misalignment for the corpus collosum and ventricles of the patient). This image misalignment may be the result of non-rigid brain shift during a surgical procedure—which rigid registration technologies have trouble accounting for. As alluded to above, where planned target and entry points for surgical trajectories are located on/within the soft tissues of a patient's brain, this misalignment can cause problems as coordinates for these planned target/entry points may shift in space with respect to their location in a pre-operative image that was used for planning.

As compared to the rigid registration techniques conventionally used in image-guided brain interventions (as depicted in the example of FIG. 2), examples can improve alignment between soft tissue images of cranial images obtained before and after non-rigid brain shift has occurred. This may include more accurate/precise mapping coordinates of planned target and entry points (located on/within the soft tissues) from a pre-operative image or brain atlas to their corresponding/appropriate locations in an intra-operative image. By more accurately/precisely mapping planned target and entry point coordinates from cranial images used for surgical trajectory planning to intra-operative images obtained during image-guided brain interventions, examples can improve safety and efficacy for the image-guided brain interventions (e.g., by ensuring that target and entry point coordinates in intra-operative images are located approximately in their planned locations), reduce surgical intervention times, etc.

Figure 3:
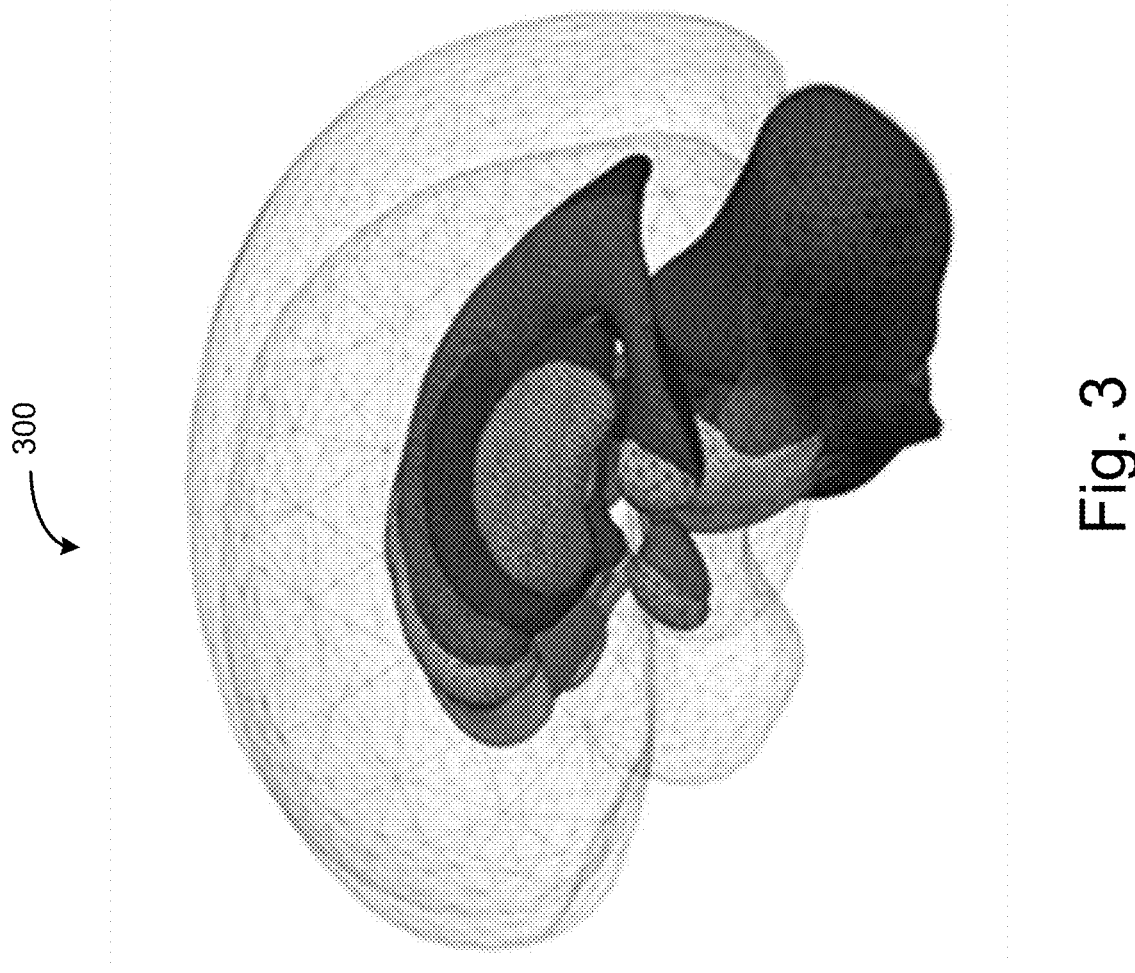
FIG. 3 depicts an example shape-constrained deformable cranial region model, in accordance with various examples of the presently disclosed technology.

FIG. 3 depicts an example shape-constrained deformable cranial region model 300, in accordance with various examples of the presently disclosed technology. Shape-constrained deformable cranial region model 300 may be a computerized 3D mesh representation of a generalized human cranial region (i.e., a non-patient-specific 3D representation of any one or combination of human scalp, skull, brain, etc.) that preserves point-based correspondences during mesh adaption to patient-specific data/images using shape-constrained deformation. Shape-constrained deformation may constrain deformation to an apriori derived mean mesh. The shape-constrained deformation can use a penalty term estimated from the mesh that prevents topological changes during mesh adaptation, which is an iterative process. Examples can start with the mean mesh and gradually deform the mean mesh to match the patient-specific data/image. In other words, shape is constrained to the mean mesh, which can grow or shrink but may not be morphed into a different shape. The mean mesh can be derived as an average mesh from a set of training data.

As alluded to above (and as will be discussed in greater detail in conjunction with FIG. 4), shape-constrained deformable cranial region model 300 can be adapted to patient-specific cranial images (e.g., pre-operative and inter-operative MR images, pre-operative and interoperative CT images, etc.) to generate patient-specific 3D mesh represen-tations. Upon generating two patient-specific 3D mesh rep-resentations (i.e., a first patient-specific 3D mesh represen-tation and a second patient-specific 3D mesh representation), examples can use correspondences between the patient-specific 3D mesh representations (e.g., "sparse" surface-based correspondences between mesh vertices of the patient-specific 3D mesh representations) to fit a non-rigid transformation function. Examples can then use the non-rigid transformation function to estimate a deformation field that provides displacement vectors for mapping points/voxels of the first cranial image to their corresponding locations/points in the second cranial image. Examples can use this deformation field to map a first cranial image to a second cranial image point-by-point/voxel-by-voxel. This may include mapping planned surgical target and entry points from the first cranial image to the second cranial image.

Referring again to FIG. 3, as depicted, shape-constrained deformable cranial region model 300 comprises mesh ele-ments and mesh vertices at the junctions of adjoining/adjacent mesh elements. Each mesh element of shape-constrained deformable cranial region model 300 may represent a different brain region. In the specific example of FIG. 3, the mesh elements of shape-constrained deformable cranial region model 300 comprise triangles, but in other examples mesh elements may comprise different shapes.

In general, a mesh may refer to a representation of a larger domain (e.g., a volume or surface) comprised of smaller discrete cells called mesh elements, and mesh vertices at the junctions of adjacent/adjoining mesh elements. Meshes can be used to compute solutions to equations across individual mesh elements, which then can be used to approximate solutions over the larger domain. As described above, examples can use "sparse" surface-based correspondences between mesh vertices of patient-specific 3D mesh repre-sentations to fit a non-rigid transformation function for estimating a deformation field that maps a first cranial image to a second cranial image point-by-point/voxel-by-voxel.

FIG. 4 depicts adaption of a shape-constrained deform-able cranial region model to two example cranial images to generate two patient-specific 3D mesh representations, in accordance with examples of the presently disclosed tech-nology.

In particular, FIG. 4 depicts a first cranial image 412 and a second cranial image 414. The cranial images may be various types of images including MR images, computerized tomography (CT) images, positron emission tomography (PET) images, brain atlases, etc. In various examples, the cranial images may be multi-modal (e.g., the first cranial image 412 may be an MR image and the second cranial image 414 may be a CT image). The cranial images may be pre-operative images (i.e., images of a patient's cranial region obtained prior to a surgical intervention into the brain), intra-operative images (i.e., images of a patient's cranial region obtained during a surgical intervention into the brain), brain atlases (i.e., generalized 3D maps of a brain), etc.

FIG. 4 also depicts a first patient-specific 3D mesh representation 422 and a second patient-specific 3D mesh representation 424. Examples may generate the first patient-specific 3D mesh representation 422 by adapting a shape-constrained deformable cranial region model (e.g., shape-constrained deformable cranial region model 300) to the first cranial image 412 using shape-constrained deformation. Similarly, examples can generate the second patient-specific 3D mesh representation 424 by adapting the shape-con-strained deformable cranial region model (e.g., shape-con-strained deformable cranial region model 300) to the second cranial image 414 (also using shape-constrained deforma-tion).

Through such adaptation, point-based correspondences can be preserved between mesh vertices of the shape-constrained deformable cranial region model and mesh vertices of the patient-specific 3D mesh representations. Such preservation can be used to establish "sparse" surface-based correspondences between mesh vertices of the first and second patient-specific 3D mesh representations 422 and 424. In other words, the "sparse" surface-based corre-spondences between mesh vertices of the first and second patient-specific 3D mesh representations 422 and 424 may be a property/function of the shape-constrained deformation process used to generate them, which adapts surface meshes to patient specific image data.

As alluded to above, examples can use "sparse" surface-based correspondences between mesh vertices of patient-specific 3D mesh representations 422 and 424 to fit a non-rigid transformation function. Examples can use the non-rigid transformation function to estimate a deformation field that provides displacement vectors for mapping points/voxels of the first cranial image 412 to their corresponding locations/points in the second cranial image 414. Examples can use this deformation field to transform/map the first cranial image 412 to the second cranial image 414 point-by-point/voxel-by-voxel—thus achieving improved align-ment between the cranial images. In certain cases, this may include transforming/mapping coordinates of planned target and entry points from the first cranial image 412 to the second cranial image 414.

FIG. 5 depicts a first example checkerboard overlay of two cranial images after rigid registration, and a second example checkerboard overlay of the two cranial images after non-rigid registration performed in accordance with the presently disclosed technology.

Here, the lighter boxes of the checkerboard overlays may depict a first cranial image and the darker boxes of the checkerboard overlay may represent a second cranial image transformed (rigidly for checkerboard overlay 510 and non-rigidly for checkerboard overlay 520) to align with the first cranial image.

As illustrated by checkerboard overlay 520, non-rigid registration performed in accordance with examples of the presently disclosed technology improves alignment between the first cranial image and the transformed second cranial image—as compared to the rigid registration illustrated by checkerboard overlay 510. In particular, the soft brain tissue images illustrated in checkerboard overlay 520 are more closely aligned than the soft brain tissue images illustrated in checkerboard overlay 510. As alluded to above, this improved soft brain tissue image alignment can be important where planned target and entry points for surgical trajecto-ries are located on/within the soft tissues of a patient's brain and coordinates for these planned target/entry points non-rigidly shift in space with respect to their location in a cranial image (e.g., a pre-operative cranial image or a brain atlas) that was used for planning.

FIG. 6 depicts an example flow diagram that may be used to non-rigidly transform a first cranial image to a second cranial image in accordance with various examples of the presently disclosed technology.

At operation 602(a), examples generate a first patient-specific 3D mesh representation based on a first cranial image. At operation 602(b), examples generate a second patient-specific 3D mesh representation based on a second cranial image.

The first and second cranial images may be various types of images including magnetic resonance (MR) images, computerized tomography (CT) images, positron emission tomography (PET) images, brain atlases, etc. The cranial images may be pre-operative images (i.e., images of a patient's cranial region obtained prior to surgery) or intra-operative images (i.e., images of a patient's cranial region obtained during a surgical intervention into the brain). In certain examples the cranial images may be multimodal (e.g., the first cranial image may be an MR image and the second cranial image may be a CT image). In some examples the first cranial image may be a cranial image used for surgical trajectory planning (e.g., a pre-operative image or a brain atlas) and the second cranial image may be an intra-operative image obtained during an image-guided intervention into a patient's brain.

As described in the previous figures, examples can generate the first and second patient-specific 3D mesh representations by adapting a shape-constrained deformable cranial region model to the first and second cranial images respectively using shape-constrained deformation. Through such adaptation, point-based correspondences can be preserved between mesh vertices of the shape-constrained deformable cranial region model and mesh vertices of the first and second patient-specific 3D mesh representations. Such preservation can later be used to establish "sparse" surface-based correspondences between mesh vertices of the first patient-specific 3D mesh representation and the second patient-specific 3D mesh representation. In other words, the "sparse" surface-based correspondences between mesh vertices of the first and second patient-specific 3D mesh representations may be a property of the shape-constrained deformation used to generate them, which adapts surface meshes to patient specific image data.

Accordingly, at operation 604 examples use correspondences between the first and second patient-specific 3D mesh representations to fit a non-rigid transformation function for estimating a deformation field that maps the first cranial image to the second cranial image. As alluded to above, the correspondences may comprise surface-based correspondences between mesh vertices of the patient-specific 3D mesh representations. Such correspondences may be termed "sparse" because the mesh vertices comprise a "sparse" subset of points of a 3D image. Where examples use this "sparse" subset of points they can perform non-rigid registrations faster than existing image intensity-based techniques which perform iterative optimizations over an entire 3D image. Also, sparse surface-based correspondence enables estimation of non-rigid transformation function in a closed loop solution. By contrast, existing image intensity-based registration methods utilize iterative optimizations, which can be slower.

The non-rigid transformation function may be represented with three volumes for X, Y, and Z coordinates respectively. A displacement vector (i.e., an (X, Y, Z) vector) may be associated with each voxel in the three 3D volumes—a given displacement vector representing an amount of deformation between the first and second patient-specific 3D mesh representations (which again are adapted from the first and second cranial images respectively). As will be described in conjunction with operation 606, these displacement vectors may be used to estimate a deformation field that can be used to map points/voxels of the first cranial image to their corresponding locations/points in the second cranial image.

At operation 606, examples use the non-rigid transformation function to estimate a deformation field. The estimated deformation field may provide displacement vectors for mapping points/voxels of the first cranial image to their corresponding locations/points in the second cranial image. In certain examples, the estimated deformation field may be a "dense" deformation field that assigns a displacement vector to each image point/voxel of the first cranial image.

At operation 608, examples use the estimated deformation field to map/transform the first cranial image to the second cranial image. In some cases, this may include mapping planned surgical target and entry point coordinates (or even entire planned surgical trajectories) from the first cranial image to the second cranial image. In certain examples, other features associated with the first cranial image may be mapped to the second cranial image (e.g., surgical tools, catheters, electrodes, etc.).

As alluded to above, the mapped (i.e., non-rigidly transformed) first cranial image may be aligned with the second cranial image. As compared to the rigid registration techniques conventionally used in image-guided brain interventions, examples can improve alignment between soft tissue images of cranial images obtained before and after non-rigid brain shift has occurred (for example, the second cranial image may be an intra-operative image obtained after non-rigid brain shift has occurred and the first cranial image may be a pre-operative image used for surgical trajectory planning—and obtained before non-rigid brain shift has occurred). Relatedly, this may include more accurate/precise mapping, from the first cranial image to the second cranial image, of planned target and entry point coordinates located on/within the soft brain tissues. By improving mapping accuracy/precision for planned target and entry point coordinates, examples can improve safety and efficacy for image-guided surgical procedures (e.g., by ensuring that target and entry point coordinates in intra-operative images are located approximately in their planned locations), reduce surgical intervention times, etc.

FIG. 7 depicts an example flow diagram that may be used to detect/estimate non-rigid brain shift during a brain intervention using an estimated deformation field, in accordance with various examples of the presently disclosed technology.

At operation 702(a), examples generate a first patient-specific 3D mesh representation based on a first cranial image. At operation 702(b), examples generate a second patient-specific 3D mesh representation based on a second cranial image. These operations may be performed in the same/similar manner as operations 602(a) and 602(b) described in conjunction with FIG. 6.

Accordingly, at operation 704 examples use correspondences between the first and second patient-specific 3D mesh representations to fit a non-rigid transformation function for estimating a deformation field that maps the first cranial image to the second cranial image. This operation may be performed in the same/similar manner as operation 604 described in conjunction with FIG. 6.

At operation 706, examples use the non-rigid transformation function to estimate a deformation field. This operation may be performed in the same/similar manner as operation 606 described in conjunction with FIG. 6.

At operation 708, examples use the estimated deformation field to estimate non-rigid brain shift. For example, based on the estimated deformation field (e.g., based on the size and location of displacement vectors used to map points/voxels of the first cranial image to their respective locations/points in the second cranial image), examples can detect non-rigid brain shift (e.g., where the size, number, or some combination of the size and number of displacement vectors exceed threshold value(s)). Here, detecting non-rigid brain shift can improve patient safety because in many cases the causes of non-rigid brain shift (e.g., CSF leakage or a change in intracranial pressure) can be harmful to the patient—and early/accurate detection may reduce patient harm. Moreover, through analysis of the estimated deformation field (e.g., analyzing the relative size and location of displacement vectors used to map points/voxels of the first cranial image to their respective locations/points in the second cranial image), examples can identify specific locations of a patient's brain impacted most by non-rigid brain shift—and by extension, locations of the patient's brain which may be most impacted by the condition that caused the non-rigid brain shift. Here, such pin-pointed detection may further improve patient safety/reduce patient harm.

Figure 8:
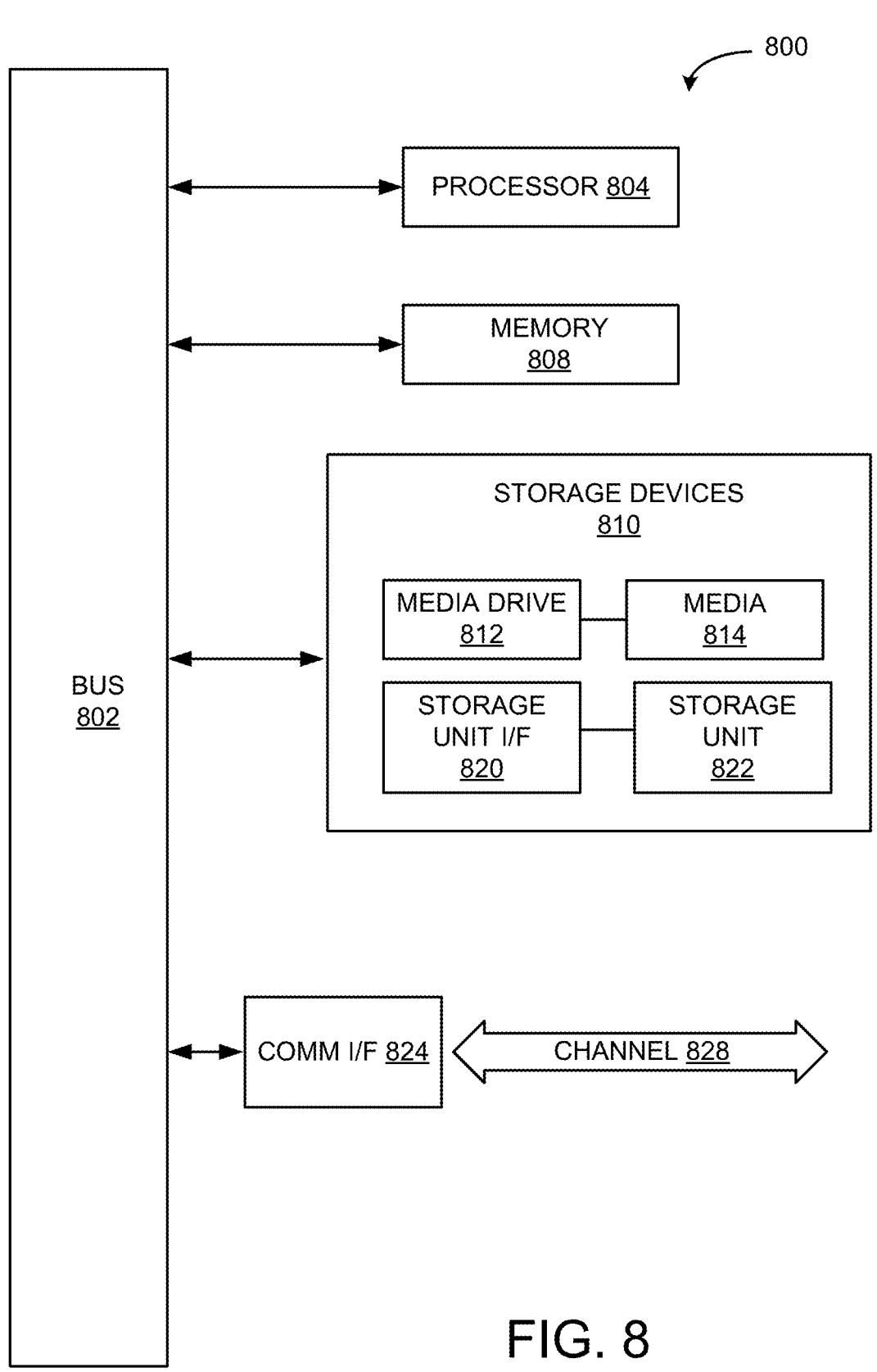
FIG. 8 is an example computing component that may be used to implement various features of examples described in the present disclosure.

As used herein, the terms circuit and component might describe a given unit of functionality that can be performed in accordance with one or more examples of the present application. As used herein, a component might be implemented utilizing any form of hardware, software, or a combination thereof. For example, one or more processors, controllers, ASICs, PLAS, PALs, CPLDs, FPGAs, logical components, software routines or other mechanisms might be implemented to make up a component. Various components described herein may be implemented as discrete components or described functions and features can be shared in part or in total among one or more components. In other words, as would be apparent to one of ordinary skill in the art after reading this description, the various features and functionality described herein may be implemented in any given application. They can be implemented in one or more separate or shared components in various combinations and permutations. Although various features or functional elements may be individually described or claimed as separate components, it should be understood that these features/functionality can be shared among one or more common software and hardware elements. Such a description shall not require or imply that separate hardware or software components are used to implement such features or functionality.

Where components are implemented in whole or in part using software, these software elements can be implemented to operate with a computing or processing component capable of carrying out the functionality described with respect thereto. One such example computing component is shown in FIG. 8. Various examples are described in terms of this examplecomputing component 800. After reading this description, it will become apparent to a person skilled in the relevant art how to implement the application using other computing components or architectures.

Referring now to FIG. 8, computing component 800 may represent, for example, computing or processing capabilities found within a self-adjusting display, desktop, laptop, note-book, and tablet computers. They may be found in hand-held computing devices (tablets, PDA's, smart phones, cell phones, palmtops, etc.). They may be found in workstations or other devices with displays, servers, or any other type of special-purpose or general-purpose computing devices as may be desirable or appropriate for a given application or environment. Computing component 800 might also represent computing capabilities embedded within or otherwise available to a given device. For example, a computing component might be found in other electronic devices such as, for example, portable computing devices, and other electronic devices that might include some form of processing capability.

Computing component 800 might include, for example, one or more processors, controllers, control components, or other processing devices. Processor 804 might be implemented using a general-purpose or special-purpose processing engine such as, for example, a microprocessor, controller, or other control logic. Processor 804 may be connected to a bus 802. However, any communication medium can be used to facilitate interaction with other components of computing component 800 or to communicate externally.

Computing component 800 might also include one or more memory components, simply referred to herein as main memory 808. For example, random access memory (RAM) or other dynamic memory, might be used for storing information and instructions to be executed by processor 804. Main memory 808 might also be used for storing temporary variables or other intermediate information during execution of instructions to be executed by processor 804. Computing component 800 might likewise include a read only memory ("ROM") or other static storage device coupled to bus 802 for storing static information and instructions for processor 804.

The computing component 800 might also include one or more various forms of information storage mechanism 810, which might include, for example, a media drive 812 and a storage unit interface 820. The media drive 812 might include a drive or other mechanism to support fixed or removable storage media 814. For example, a hard disk drive, a solid-state drive, a magnetic tape drive, an optical drive, a compact disc (CD) or digital video disc (DVD) drive (R or RW), or other removable or fixed media drive might be provided. Storage media 814 might include, for example, a hard disk, an integrated circuit assembly, magnetic tape, cartridge, optical disk, a CD or DVD. Storage media 814 may be any other fixed or removable medium that is read by, written to or accessed by media drive 812. As these examples illustrate, the storage media 814 can include a computer usable storage medium having stored therein computer software or data.

In alternative examples, information storage mechanism 810 might include other similar instrumentalities for allowing computer programs or other instructions or data to be loaded into computing component 800. Such instrumentalities might include, for example, a fixed or removable storage unit 822 and an interface 820. Examples of such storage units 822 and interfaces 820 can include a program cartridge and cartridge interface, a removable memory (for example, a flash memory or other removable memory component) and memory slot. Other examples may include a PCMCIA slot and card, and other fixed or removable storage units 822 and interfaces 820 that allow software and data to be transferred from storage unit 822 to computing component 800.

Computing component 800 might also include a communications interface 824. Communications interface 824 might be used to allow software and data to be transferred between computing component 800 and external devices. Examples of communications interface 824 might include a modem or softmodem, a network interface (such as Ethernet, network interface card, IEEE 802.XX or another interface). Other examples include a communications port (such as for example, a USB port, IR port, RS232 port Bluetooth® interface, or other port), or another communications interface. Software/data transferred via communications interface 824 may be carried on signals, which can be electronic, electromagnetic (which includes optical) or other signals capable of being exchanged by a given communications interface 824. These signals might be provided to communications interface 824 via a channel 828. Channel 828 might carry signals and might be implemented using a wired or wireless communication medium. Some examples of a channel might include a phone line, a cellular link, an RF link, an optical link, a network interface, a local or wide area network, and other wired or wireless communications channels.

In this document, the terms "computer program medium" and "computer usable medium" are used to generally refer to transitory or non-transitory media. Such media may be, e.g., memory 808, storage unit 820, media 814, and channel 828. These and other various forms of computer program media or computer usable media may be involved in carrying one or more sequences of one or more instructions to a processing device for execution. Such instructions embodied on the medium, are generally referred to as "computer program code" or a "computer program product" (which may be grouped in the form of computer programs or other groupings). When executed, such instructions might enable the computing component 800 to perform features or functions of the present application as discussed herein.

It should be understood that the various features, aspects and functionality described in one or more of the individual examples are not limited in their applicability to the particular example with which they are described. Instead, they can be applied, alone or in various combinations, to one or more other examples, whether or not such examples are described and whether or not such features are presented as being a part of a described example. Thus, the breadth and scope of the present application should not be limited by any of the above-described exemplary examples.

Terms and phrases used in this document, and variations thereof, unless otherwise expressly stated, should be construed as open ended as opposed to limiting. As examples of the foregoing, the term "including" should be read as meaning "including, without limitation" or the like. The term "example" is used to provide exemplary instances of the item in discussion, not an exhaustive or limiting list thereof. The terms "a" or "an" should be read as meaning "at least one," "one or more" or the like; and adjectives such as "conventional," "traditional," "normal," "standard," "known." Terms of similar meaning should not be construed as limiting the item described to a given time period or to an item available as of a given time. Instead, they should be read to encompass conventional, traditional, normal, or standard technologies that may be available or known now or at any time in the future. Where this document refers to technologies that would be apparent or known to one of ordinary skill in the art, such technologies encompass those apparent or known to the skilled artisan now or at any time in the future.

The presence of broadening words and phrases such as "one or more," "at least," "but not limited to" or other like phrases in some instances shall not be read to mean that the narrower case is intended or required in instances where such broadening phrases may be absent. The use of the term "component" does not imply that the aspects or functionality described or claimed as part of the component are all configured in a common package. Indeed, any or all of the various aspects of a component, whether control logic or other components, can be combined in a single package or separately maintained and can further be distributed in multiple groupings or packages or across multiple locations.

Additionally, the various examples set forth herein are described in terms of exemplary block diagrams, flow charts and other illustrations. As will become apparent to one of ordinary skill in the art after reading this document, the illustrated examples and their various alternatives can be implemented without confinement to the illustrated examples. For example, block diagrams and their accompanying description should not be construed as mandating a particular architecture or configuration.

What is claimed is:

1. A method, comprising:
    adapting a shape-constrained deformable cranial region model to a first cranial image to generate a first patient-specific 3D mesh representation;
    adapting the shape-constrained deformable cranial region model to a second cranial image to generate a second patient-specific 3D mesh representation;
    using correspondences between the first and second patient-specific 3D mesh representations to fit a non-rigid transformation function;
    estimating a deformation field using the non-rigid transformation function;
    detecting non-rigid brain shift in a patient responsive to determining at least one of the following:
        length of at least one displacement vector of the estimated deformation field exceeds a threshold length value, or
        over a threshold number of displacement vectors of the estimated deformation field have lengths exceeding the threshold length value;
    mapping coordinates of planned target points and entry points in the first cranial image to corresponding locations in the second cranial image using the estimated deformation field; and
    displaying, on a graphical user interface (GUI), a visual representation of the second cranial image overlaid with:
        visual highlights for the mapped planned target points and entry points at their corresponding locations in the second cranial image, and
        a visual warning indicating the detected non-rigid brain shift.

2. The method of claim 1, wherein the correspondences between the first and second patient-specific 3D mesh representations comprise surface-based correspondences between mesh vertices of the first and second patient-specific 3D mesh representations.

3. The method of claim 1, wherein the first cranial image is a pre-operative image of a patient's cranial region used for surgical trajectory planning and the second cranial image is an intra-operative image of the patient's cranial region obtained during a surgical intervention into the patient's cranial region.

4. The method of claim 1, wherein the first cranial image is a brain atlas used for surgical trajectory planning and the second cranial image is an intra-operative image of a patient's cranial region obtained during a surgical intervention into the patient's cranial region.

5. The method of claim 1, wherein the shape-constrained deformable cranial region model comprises a computerized 3D mesh representation of a non-patient-specific human cranial region that preserves point-based correspondences during mesh adaption to patient images.

6. The method of claim 1, wherein the first and second cranial images comprise at least one of the following types of images:

a magnetic resonance (MR) image;

a computerized tomography (CT) image; and a positron emission tomography (PET) image.

7. The method of claim 6, wherein the first and second cranial images comprise different types of images.

8. The method of claim 1, wherein the estimated deformation field is a dense deformation field comprising an individual displacement vector associated with each voxel of the first cranial image, the displacement vectors mapping voxels of the first cranial image to corresponding voxels of the second cranial image.

9. Non-transitory computer-readable storage medium including instructions that, when executed by one or more processors of a computing system, cause the computing system to:

adapt a shape-constrained deformable cranial region model to a first cranial image to generate a first patient-specific 3D mesh representation;

adapt the shape-constrained deformable cranial region model to a second cranial image to generate a second patient-specific 3D mesh representation;

use surface-based correspondences between mesh vertices of the first and second patient-specific 3D mesh representations to fit a non-rigid transformation function;

estimate a deformation field using the non-rigid transformation function;

detect non-rigid brain shift in a patient responsive to determining at least one of the following:

length of at least one displacement vector of the estimated deformation field exceeds a threshold length value, or over a threshold number of displacement vectors of the estimated deformation field have lengths exceeding the threshold length value;

map planned surgical target point and entry point coordinates from the first cranial image to the second cranial image using the estimated deformation field; and display, on a graphical user interface (GUI), a visual representation of the second cranial image overlaid with:

visual highlights for the mapped planned target points and entry points at their corresponding locations in the second cranial image, and a visual warning indicating the detected non-rigid brain shift.

10. The non-transitory computer-readable medium of claim 9, wherein the first cranial image is a pre-operative image of a patient's cranial region used for surgical trajectory planning and the second cranial image is an intra-operative image of the patient's cranial region obtained during a surgical intervention into the patient's cranial region.

11. The non-transitory computer-readable medium of claim 9, further comprising instructions that, when executed by the one or more processors, cause the computing system to map the first cranial image to the second cranial image.

12. The non-transitory computer-readable medium of claim 11, wherein the estimated deformation field is a dense deformation field comprising an individual displacement vector associated with each voxel of the first cranial image including voxels associated with the planned surgical target point and entry point coordinates, the displacement vectors mapping voxels of the first cranial image to corresponding voxels of the second cranial image.

13. The non-transitory computer-readable medium of claim 1, wherein the shape-constrained deformable cranial region model comprises a computerized 3D mesh representation of a non-patient-specific human cranial region that preserves point-based correspondences during mesh adaption to patient images.

14. The non-transitory computer-readable medium of claim 9, wherein the first and second cranial images comprise at least one of the following types of images:

a MR image;

a CT image; and a PET image.

15. The non-transitory computer-readable medium of claim 13, wherein the first and second cranial images comprise different types of images.

16. A system comprising:

one or more processing resources; and non-transitory computer-readable medium, coupled to the one or more processing resources, having stored therein instructions that when executed by the one or more processing resources cause the system to:

adapt a shape-constrained deformable cranial region model to a first cranial image to generate a first patient-specific 3D mesh representation;

adapt the shape-constrained deformable cranial region model to a second cranial image to generate a second patient-specific 3D mesh representation;

use correspondences between mesh vertices of the first and second patient-specific 3D mesh representations to fit a non-rigid transformation function;

estimate deformation field using the non-rigid transformation function;

detect non-rigid brain shift in a patient responsive to determining at least one of the following:

length of at least one displacement vector of the estimated deformation field exceeds a threshold length value, or over a threshold number of displacement vectors of the estimated deformation field have lengths exceeding the threshold length value; and display, on a graphic user interface (GUI), a visual warning indicating the detected non-rigid brain shift.

17. The system of claim 16, wherein:

the estimated deformation field is a dense deformation field comprising an individual displacement vector associated with each voxel of the first cranial image, the displacement vectors mapping voxels of the first cranial image to corresponding voxels of the second cranial image; and estimating non-rigid brain shift in the patient comprises determining magnitudes of displacement vectors of the estimated deformation field.

18. The system of claim 16, wherein the shape-constrained deformable cranial region model comprises a computerized 3D mesh representation of a non-patient-specific human cranial region that preserves point-based correspondences during mesh adaption to patient images.

19. The system of claim 16, wherein the correspondences between the first and second patient-specific 3D mesh representations comprise surface-based correspondences between mesh vertices of the first and second patient-specific 3D mesh representations.

20. The system of claim 16, wherein the visual warning indicating the detected non-rigid brain shift overlays the second cranial image of the second patient-specific 3D mesh representation.

* * * * *